(12) United States Patent
Strano et al.

(10) Patent No.: US 12,419,720 B2
(45) Date of Patent: Sep. 23, 2025

(54) MULTIMODALITY ID MARKERS FOR DELINEATING THE POSITION OF A REGION OF INTEREST (ROI) WITHIN A BODY

(71) Applicant: SPRINGLOC LTD., Hosen (IL)

(72) Inventors: Shalom Strano, Jerusalem (IL); Alexander Lomes, Moshav Hosen (IL); Steve Krupa, Haifa (IL)

(73) Assignee: SPRINGLOC LTD., Hosen (IL)

( * ) Notice: Subject to any disclaimer, the term of this patent is extended or adjusted under 35 U.S.C. 154(b) by 327 days.

(21) Appl. No.: 17/724,487

(22) Filed: Apr. 19, 2022

(65) Prior Publication Data

US 2022/0338953 A1    Oct. 27, 2022

Related U.S. Application Data

(60) Provisional application No. 63/231,243, filed on Aug. 10, 2021, provisional application No. 63/179,893, filed on Apr. 26, 2021.

(51) Int. Cl.
*A61B 90/00* (2016.01)
*A61B 90/98* (2016.01)

(52) U.S. Cl.
CPC .............. *A61B 90/39* (2016.02); *A61B 90/98* (2016.02); *A61B 2090/3925* (2016.02); *A61B 2090/3937* (2016.02); *A61B 2090/3966* (2016.02); *A61B 2090/3983* (2016.02); *A61B 2090/3995* (2016.02)

(58) Field of Classification Search
CPC . A61B 90/39; A61B 90/98; A61B 2090/3925; A61B 2090/3937; A61B 2090/3966; A61B 2090/3983; A61B 2090/3995
See application file for complete search history.

(56) References Cited

U.S. PATENT DOCUMENTS

| | | |
|---|---|---|
| 8,892,185 B2 | 11/2014 | Sing et al. |
| 8,973,584 B2 | 3/2015 | Brander et al. |
| 9,386,942 B2 | 7/2016 | Chi et al. |
| 9,646,423 B1 | 5/2017 | Sun et al. |
| 9,713,437 B2 | 7/2017 | Fullerton et al. |

(Continued)

FOREIGN PATENT DOCUMENTS

| | | |
|---|---|---|
| EP | 2996555 B1 | 3/2016 |
| WO | 2017066372 A1 | 4/2017 |

OTHER PUBLICATIONS

Notice of Allowance for U.S. Appl. No. 17/841,663 mailed Oct. 30, 2024.

(Continued)

*Primary Examiner* — Chao Sheng
(74) *Attorney, Agent, or Firm* — Ballard Spahr LLP

(57) ABSTRACT

Multimodality markers for delineation of a region of interest (ROI) within a patient's body are disclosed. The markers may comprise a hermetic bio-compatible container and an external element that is associated with the hermetic bio-compatible container. A unique collective identification (ID) is assigned to each of the markers. The collective ID can comprise a visible component seen on an imaging system (Continued)

and an electronic component stored in a microelectronic chip and embedded within the hermetic bio-compatible container.

20 Claims, 2 Drawing Sheets

(56) References Cited

U.S. PATENT DOCUMENTS

| | | | |
|---|---|---|---|
| 9,730,764 | B2 | 8/2017 | Van Der Weide et al. |
| 9,867,550 | B2 | 1/2018 | Brander et al. |
| 9,987,097 | B2 | 6/2018 | Van Der Weide et al. |
| 10,154,799 | B2 | 12/2018 | Van Der Weide et al. |
| 10,278,779 | B1 | 5/2019 | Rudie et al. |
| 10,326,975 | B2 | 6/2019 | Casas |
| 10,383,544 | B2 | 8/2019 | Fullerton et al. |
| 10,646,303 | B1 | 5/2020 | Strano et al. |
| 10,751,145 | B2 | 8/2020 | Van Der Weide et al. |
| 10,827,949 | B2 | 11/2020 | Greene et al. |
| 10,849,529 | B2 | 12/2020 | Brander et al. |
| 10,854,799 | B2 | 12/2020 | Tanabe |
| 10,970,862 | B1 | 4/2021 | Na et al. |
| 2005/0279963 | A1 | 12/2005 | Church et al. |
| 2011/0021888 | A1* | 1/2011 | Sing .............. A61B 5/0507 600/562 |
| 2014/0309522 | A1* | 10/2014 | Fullerton ............ A61B 90/39 600/424 |
| 2016/0051164 | A1 | 2/2016 | Derichs et al. |
| 2018/0125389 | A1 | 5/2018 | Brander et al. |
| 2018/0279907 | A1* | 10/2018 | Greene .............. H01Q 1/002 |
| 2019/0150779 | A1 | 5/2019 | Derichs et al. |
| 2019/0223975 | A1 | 7/2019 | Agostinelli et al. |
| 2019/0365279 | A1 | 12/2019 | Fullerton et al. |
| 2020/0409306 | A1 | 12/2020 | Gelman et al. |
| 2021/0100476 | A1 | 4/2021 | Brander et al. |
| 2021/0169579 | A1* | 6/2021 | Laviola ............... A61B 34/20 |
| 2022/0338953 | A1 | 10/2022 | Strano et al. |

OTHER PUBLICATIONS

Restriction Requirement for U.S. Appl. No. 17/841,663 mailed May 22, 2024.
U.S. Appl. No. 63/179,893, filed Apr. 26, 2021.
U.S. Appl. No. 63/231,243, filed Aug. 10, 2021.
"FCC Online Table of Frequency Allocations", Federal Communications Commission Office of Engineering and Technology Policy and Rules Division, Jul. 1, 2022, pp. 1-180.
"LOCalizer Wire-Free Guidance System", Hologic Inc. Breast Surgery Portfolio https://hologicbreastsurgery.com/en/portfolio/localizer-wire-free-guidance-system/ last accessed Jan. 28, 2025, pp. 1-3.
"NTAG 203 NFC Forum Type 2 Tag Compliant IC With 144 Bytes User Memory", NXP Semiconductors; Product Data Sheet Rev. 3.0; https://cdn-shop.adafruit.com/productfiles/4034/P4034_datasheet_NTAG_203.pdf last accessed Jan. 28, 2025, Oct. 17, 2011, pp. 1-30.
Harrison, et al., "A 60 GHz Analog Phase Shifter in 65 NM Bulk CMOS Process", International Journal of Computer Networks & Communications (IJCNC); vol. 2, No. 4, Jul. 2010, pp. 13-20.
Stolik, et al., "Measurement of the Penetration Depths of Red and Near Infrared Light in Human "Ex Vivo" Tissues", Journal of Photochemistry and Photobiology B: Biology; vol. 57, Issues 2-3, Sep. 2000, pp. 90-93.
Yan, et al., "Optimization of Output Power and Transmission Efficiency of Magnetically Coupled Resonance Wireless Power Transfer System", AIP Advances; Research Article, Magnetism and Magnetic Materials https://doi.org/10.1063/1.5007276 last accessed Jan. 28, 2025, Jan. 2, 2018, pp. 056625-1-056625-6.
Notice of Allowance for U.S. Appl. No. 18/083,565 mailed May 2, 2025.
U.S. Appl. No. 17/724,487, filed Apr. 19, 2022.
U.S. Appl. No. 17/841,663, filed Jun. 16, 2022.
U.S. Appl. No. 63/218,973, filed Jul. 7, 2021.
U.S. Appl. No. 63/293,643, filed Dec. 23, 2021.

* cited by examiner

MULTIMODALITY ID MARKERS FOR DELINEATING THE POSITION OF A REGION OF INTEREST (ROI) WITHIN A BODY

CROSS-REFERENCE TO RELATED APPLICATIONS

This utility patent application being filed in the United States as a non-provisional application for patent, claiming the benefit of the prior filing date under Title 35, U.S.C. § 119(e) of the U.S. provisional application for patent that was filed on Apr. 26, 2021 and assigned the Ser. No. 63/179,893 and the U.S. provisional application for patent that was filed on Aug. 10, 2021 and assigned the Ser. No. 63/231,243, which applications are herein incorporated by reference in their entirety.

FIELD OF THE DISCLOSURE

The present disclosure relates to the field of marking positions of body structures in-vivo accurately, in order to facilitate further pathological, diagnostic, surgical or therapeutic procedures. The main feature of our approach employs markers with differing unique collective identifiable (ID) features where such features are discretely identifiable on differing imaging systems such as for example mammography, X-ray, MRI, CT and ultrasound.

BACKGROUND

A common and serious challenge in many medical instances is the accurate localization of sites and lesions requiring monitoring or treatment. An example for treatment can be such as but not limited to surgical removal of those lesions. After imaging of a body tissue, whether by mammography, ultrasound, Magnetic-Resonance-Imaging (MRI) system, Computed-Tomography scan (CT) or any other imaging system, there may be a need to mark one or more regions of interest (ROI). The ROI can be a foreign body, suspected tumor, or other lesion, etc. Marking the ROI is needed in order to convey to the medical personal the place/s that may need further examination/s or further treatment such as but not limited to surgery.

Marking of the ROI may be achieved with devices such as wires or markers of different types. The markers, by being attached, placed within or in close proximity to the ROI, may physically mark the position for observation, surgery or for irradiation by an electron or proton accelerator etc.

As the markers may move or migrate within the body from the time of first placement, it is important; that the marker is secured to the body tissue and to be able to visualize and confirm its accurate position with imaging systems such as X-Ray, ultrasound or MRI.

In the case of surgeries and medical procedures for non-palpable lesions, physicians may have trouble locating a target prior to and during its removal or manipulation. Examples of this include the removal of masses, fluid collections, foreign bodies or diseased tissues etc. Furthermore, catheter and tube placement, or other percutaneous procedures are often performed either without direct visualization or with the lack of a specific guidance. Performing procedures without precise guidance may result in the removal of unnecessary excess tissue, increase the amount of damage to normal tissue and decrease the patient's functional status. In the present disclosure and the claims, the terms masses, fluid collections, foreign bodies, diseased tissues, tumor, polyp, or lesions may be used interchangeably.

An existing method of localizing non palpable lesions, especially in the case of breast lesions, is with a hook-wire localization device. The wire is housed within an introducer needle which is placed percutaneously under imaging guidance close to or within the ROI. The distal end of the wire comprises a hook, which is deployed by the radiologist once the wires' correct position is established. This hook fixates the wire in position and minimizes its migration from the lesion. The wire extends through the skin to the lesion within the breast or body tissue in question and acts as a mechanical guide for the surgeon to reach the target. Often more than one guide wire is needed in order to define or bracket the extent of the lesion to be surgically removed.

However, this localization procedure is painful. The wire extending through the skin is uncomfortable and requires bending and strapping to the skin in order to avoid dislodgement and migration. This is particularly problematic if the wire is left in overnight. In addition, the hook-wire localization techniques are technically challenging to perform, time consuming, painful and provide the surgeon with suboptimal guidance.

In order to overcome the disadvantages of hook-wire localization wires, other localization devices have been developed. These utilize small markers, placed or contained within the lumen of an introducer needle and inserted percutaneously under image guidance into or close to the ROI. Once deployed, these markers are activated or respond to a signal and are located with a locating device which may be machine, robotic, endoscopically or hand held/guided, for example. These locating devices enable the surgeon intraoperatively to locate the marker or markers and hence localize the ROI.

Further systems incorporating an implanted marker and located with a locator include; a marker configured to emit a radio frequency (RF) signal at predefined frequencies; a marker activated or responsive to a magnetic field wherein the magnetic field is generated by a remote activating device and a marker system detected by triangulation and located with a combined hand-held locator and surgical cutting device. A further system involves implanting an infra-red (IR) activated microwave reflector. These markers of differing—design activated or responsive to a plurality of signals are referred to as multimodality marker systems.

These multimodality marker systems include radio opaque markers to facilitate confirmation of their presence on imaging. Some marker bodies can have material surface or shape features that cause the markers to respond in vivo uniquely one from the other to an interrogating/localizing signal, thereby assisting in their unique localization at surgery. Some have associated struts or fasteners to keep them in place. The above features are essentially functional for in vivo detection and to prevent marker migration. They do not unequivocally distinguish each system's markers, one from the other at imaging and more specifically at mammography. In instances where multiple markers have been placed in a single anatomical region, for example in one breast, existing systems do not have the ability to assign a different unique collective identity to each of the multiple markers which co-exist and are seen simultaneously on imaging systems. Imaging systems such as but not limited to X-Ray mammography, etc.

Accordingly, further apparatus and methods for the designation and localization of foreign bodies, lesions or other tissue structures in order to facilitate further pathological, diagnostic, surgical or therapeutic procedures are needed and would be useful.

BRIEF SUMMARY

The needs and the deficiencies that are described above are not intended to limit the scope of the inventive concepts of the present disclosure in any manner. The needs are presented for illustration only. The disclosure is directed to a novel technique for localizing lesions within a patient's body, e.g., within a breast.

The disclosed technique employs markers, each with unique identifiable features, ID features, where the markers are placed, attached to or implanted (for example via a needle) into or in the region of the surgical ROI(s) and activated by a signal, for example but not limited to a Infra-red or RFID code signal or electromagnetic signal. Some markers are not activated but rather respond to a signal. The disclosed technique allows the surgeon to individually track and locate each one of the implanted markers providing the ability for the more accurate delineation and removal of the surgical ROI(s). The markers can also be used to uniquely identify lesions requiring targeted follow up observation or therapy.

Furthermore, the body of the marker can be uniquely identified by an imaging system, such as but not limited to an X-Ray, by attaching radio opaque material to the body of the marker, for example. The radio opaque material can be attached to the inner surface of the marker. Alternatively, the radio opaque material can be attached to the outside surface of the marker. The radio opaque material can be in the form of shapes numbers, symbols, etc. An example of such a shape can be one or more circles, wherein the number of circles represents a component of the unique collective ID of that marker. In addition, some embodiments of the markers can have one or more antenna with a plurality of shapes, for example, in the form of a spring, shaped co-linearly or offset by using a "kinked" (pre-bent) spring connector. The above disclosed type of IDs can be referred as visible ID (VID).

The VID of each marker can be established by at least one feature from a group of features. Some examples of VID features can include; radio opaque markings, antennae shape, the shape of an attached external-identification-element (EIE), unique ridges on the markers surface, unique interspaced gaps in the markers metallic coil windings and attached rings and clips for example.

Some embodiments of the markers can be associated with one or more external-identification-elements (EIE). Some embodiments of the EIE can have a plurality of shapes. An example of EIE can be in the form of a spring shaped co-linearly or offset by using a "kinked" (pre-bent) spring connector. Some embodiments may use a fixed spring; other embodiments may use a retractable expandable spring. In some embodiments the spring can be used as an identifier of the markers ID. Some embodiments of the markers may use a pair of joint-markers. The joint-markers are self-anchored by a retractable/expendable or fixed spring. The EIE can be built from bio-compatible diamagnetic metal, nitinol or tungsten for example. The EIE can be attached to the marker and act as fixing element that prevents migration.

The uniquely identifiable component of the marker can be seen with an ultrasound system. Such an example marker and/or its VID can be coated with a suitable material to enhance the visualization of the marker and the VID. An example of suitable material can be a hydrophilic material such as but not limited to hydro gel material.

The markers can have a microelectronic chip, for example an RFID chip. Each marker can be associated with a unique electronic ID code that is stored in a memory of the microelectronic chip. The stored ID code can form part of the unique collective ID of that marker. The markers VID can also be expressed by the external shape of the marker, its antenna/e, its associated EIE/s or its radio opaque marking. All the forms of ID designation of each marker can be correlated and combined so as to jointly characterize each marker's unique collective ID.

Some embodiments of the disclosed technique can be implanted via an introducer needle. In addition, some embodiments can have their antennae's and/or EIE's prebent, folded or made of a memory material, within the lumen of the introducer wherein they assume their unique shape and orientation on deployment.

The foregoing summary is not intended to summarize each potential embodiment or every aspect of the present invention, and other features and advantages of the present invention will become apparent upon reading the following detailed description of example embodiments with the accompanying drawings and appended claims.

Furthermore, although specific embodiments are described in detail to illustrate the inventive concepts to a person skilled in the art, such embodiments can be modified to various modifications and alternative forms. Accordingly, the figures and written description are not intended to limit the scope of the inventive concepts in any manner.

Other objects, features, and advantages of the disclosed apparatuses will become apparent upon reading the following detailed description of example embodiments with the accompanying drawings and appended claims.

BRIEF DESCRIPTION OF THE DRAWINGS

Example embodiments of the present disclosure will be understood and appreciated more fully from the following detailed description, taken in conjunction with the drawings in which.

DETAILED DESCRIPTION OF SOME EXAMPLE EMBODIMENTS

Turning now to the figures in which like numerals represent like elements throughout the several views, in which exemplary embodiments of the disclosed techniques are described. For convenience, only some elements of the same group may be labeled with numerals.

The purpose of the drawings is to describe examples of embodiments and not for production purpose. Therefore, features shown in the figures are chosen for convenience and clarity of presentation only and are not necessarily shown to scale. Moreover, the language used in this disclosure has been principally selected for readability and instructional purposes, and may not have been selected to define or limit the inventive subject matter.

In this specification, these implementations, or any other form that the invention may take, may be referred to as techniques. In general, the order of the steps of disclosed processes may be altered within the scope of the invention. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

In the following description, the words "unit," "element," "module", and "logical module" may be used interchangeably. Anything designated as a unit or module may be a stand-alone unit or a specialized or integrated module. A unit or a module may be modular or have modular aspects allowing it to be easily removed and replaced with another similar unit or module. Each unit or module may be any one of, or any combination of, hardware configured to execute the task ascribed to the unit or module. In the present disclosure the terms task, method, and process can be used interchangeably. In addition, the terms element and section can be used interchangeably.

Figure 1:
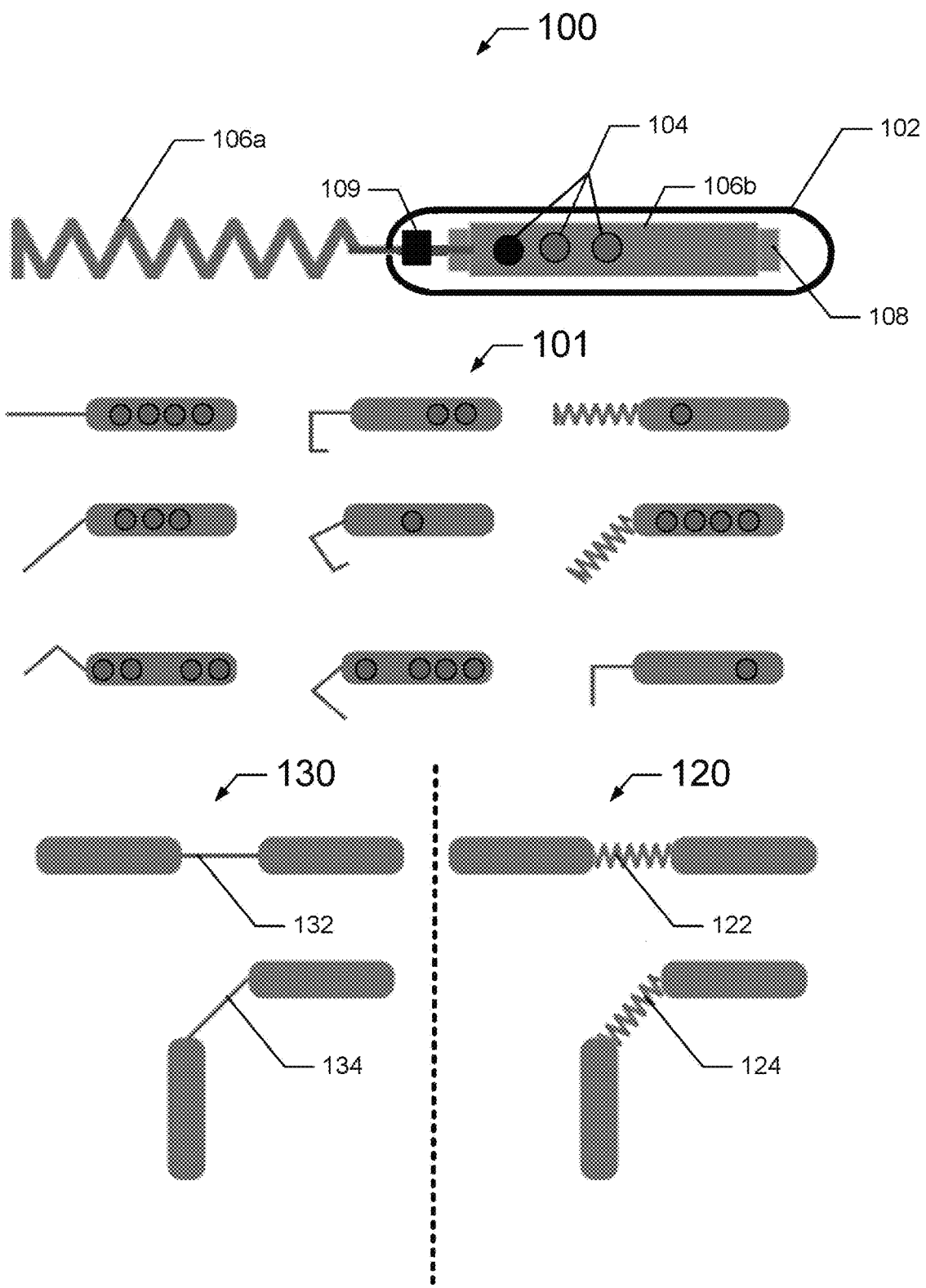
FIG. 1 schematically illustrates examples of different mechanical assemblies of markers.

FIG. 1 schematically illustrates relevant elements of examples of different mechanical assemblies of markers. An example of marker 100 may comprise a microelectronic chip 109, a dipole antenna 106a and 106b, an electromagnetic antenna 108, a hermetic bio-compatible container 102, and unique visual ID symbols (VID) 104. Examples of hermetic bio-compatible container 102 can be made of bio-compatible dielectric material, such as but not limited to glass and/or plastic. In some examples of marker 100, element 106a may not serve as antenna but is used as an EIE, which is attached to the hermetic bio-compatible container 102. In such embodiment, element 106a is not electrically connected to the microelectronic chip 109. Yet, in some embodiments of a marker 100, the antenna and the EIE can be simultaneously attached to the body of the marker 102.

In some embodiments of marker 100 the VID of the marker/s can be designated by varying uniquely identifiable radio opaque identification markings 104. Markings 104 can be such as but not limited to shapes, letters or numbers on or within the receptacle capsule of the marker. In some embodiments of marker 100 the VID of the marker/s can be designated by unique ridges on the markers surface, unique interspaced gaps in the markers metallic coil windings and attached rings and clips (not shown) for example. In some embodiments of marker 100 the VID of the marker/s can be designated by varying the physical appearance or geometric bended shape of the marker and or the shape of an element, which can be an external antenna and/or an EIE, which are attached to the container 102. Both the above types being visible with imaging modalities such as but not limited to X-Ray and mammography. Further, a part of the unique collective ID of the marker 100 can be a unique electronic ID that is stored in the microelectronic chip 109. The VID of each marker can be established by at least one feature from a group of features including for example; radio opaque markings, antennae shape, the shape of an attached external-identification-element (EIE), unique ridges on the markers surface, unique interspaced gaps in the markers metallic coil windings and attached rings and clips.

Furthermore, the VID of the markers can be correlated with their electronic identification. For example, a specific marker visualized on a mammogram X-Ray can be identified by the unique radio opaque markings 104 of its encasement and by the unique shape of its external antenna and or its EIE as well as by its unique electronic ID that was stored in the microelectronic chip 109 prior to its placement in the body tissue. All the forms of ID designation of each marker can be correlated and combined so as to characterize each marker's unique collective ID.

The identifying features described above are also applicable to other marker designs that can be detected by a plurality of signals (i.e, with multimodality systems). For example, some example embodiments may comprise a receptacle capsule (not shown in the figures) without any external antenna but with one or more attached EIEs. Other example embodiments of a marker may comprise a capsule 102 and one or more external antenna. Other embodiments of a marker may comprise reflective material such as but not limited to metal or combination of metals with attached external EIE/s. Further example embodiments of a marker may embody a unique electronic ID being neither in the form of a capsule or a pellet. Such embodiment can be associated with an electronic card that stores the unique electronic ID of the marker. Such embodiment can be associated with an EIE. Any combination of the above methods can be used to characterizing the unique collective ID of markers of multiple designs detected by a plurality of signals. Markers with different unique collective ID's may be combined to constitute a system of markers.

The VID of each marker can be established for example as follows. In the case of markers with a receptacle capsule or electronic card, the above described uniquely identifying radio opaque markings 104 would be applicable. In cases where antenna/e 106a and or EIE are present, the physical appearance or geometric bended shape of the marker and or the external antenna 106a and or the EIE attached to the marker would be applicable. In the case of the marker being comprised of a reflective material with attached EIE, the physical appearance or geometric bended shape of the marker and or the EIEs attached to the marker would be applicable in designating the visible identity of the marker. Combinations of the above described markers and identifying features may be applicable too.

When a single marker has been placed in a body of tissue, for example in a breast, and delineates an ROI, the confirmation of removal of the marker is established by performing an X-Ray of the excised surgical specimen. This may be done in the operating room. The operator may also use a hand held detector, scan over the specimen and with a locator system confirm the presence of the marker within it.

However, there are instances where multiple markers are used to delineate the ROI. Furthermore, there can be instances where additional markers unrelated to the ROI and not requiring surgical excision may be present in one breast, for example. The medical records should contain the information of each markers placed position and corresponding electronic ID. However, when multiple markers with a like appearance at imaging system are reviewed, it can be extremely challenging to accurately correlate each marker as seen on the mammogram with its own recorded electronic ID. This problem is compounded when there is evidence of marker migration and the specific marker needs to be identified on the mammogram. Successful removal of a marker is not an automatic confirmation of removal of the ROI.

For example, three markers, each with a registered unique electronic ID may be cited in the records as being placed at 2 o'clock in the left breast. The recorded data is often insufficient for the operator to be quite sure as to which of the three markers the three registered electronic IDs belong. They are all at 2 o'clock and they all look alike or almost alike on the mammogram. In such a setting, a plurality of marker features identifiable on mammography can be extremely helpful. Since the three markers at 2 o clock may now have different unique encasement and/or antenna and/or EIE features, and since they can be visually uniquely differentiated one from the other, and since their correlating unique electronic ID's are known, the operator is more empowered to establish which markers are related to the ROI and require excision and which can be left in place. The operator can more comprehensively plan the surgical procedure.

Following the localization and removal of the markers and presumably the associated ROI, the surgical specimen can be X-rayed and scanned with a hand-held locator. In this instance, apart from the electronic ID's established by the locator, the X-Ray will confirm to the surgeon that the desired marker/s from the 2 o'clock area of the left breast has/have been removed. This is established by comparing the visible ID features of the markers in the specimen X-Ray with the visible marker features on the pre-operative mammogram. This is especially helpful in the event of the locator and the localization system failing at surgery to locate the marker/s.

The visible ID's also allow for the identification and follow up of non-palpable lesions which having undergone image guided biopsies and marked at the time of biopsy and are only subsequently found to be benign and not requiring excision. These lesions can then be uniquely identified for example at mammography and hence with confidence identified for targeted follow up.

For example, the visual ID of the presented marker 100 is comprised by three dots/circles 104 made of radio opaque material, as well as by the shape of the radio opaque external antenna 106a which in this illustration is in the form of a spring. The material comprising the radio opaque markings may be silver or tungsten, for example. The external antenna and or the attached EIE/s (not shown) may be of tungsten or nitinol or a combination of appropriate metals. For example, the material can be a memory metal.

An example group 101 demonstrates several markers in which the external antenna or the attached EIE has a unique shape. The unique shape can represent part of the unique collective ID that was allocated to that marker. The external antenna or the attached EIE can be made of metal that can be visible by imaging devices such as but not limited to X-Ray, CT, ultra-sound (US), etc. The metal can be tungsten or nitinol, for example. In some embodiments the external antenna with its unique shape may be an external pole 106a of a dipole antenna 106a & 106b. In other embodiments, one or more external antenna with unique shapes may be part of a marker that is configured to be located with an infra-red signal.

The example group 101 illustrates marker encasements with various numbers of radio opaque markings 104, in this case dots and or circles, which by way of their number/configuration further characterize the visual ID of the markers, for example. The markers' unique electronic ID is stored in the microelectronic chip 109. The external antenna and or the attached EIE can be made of metal that can be visible by imaging devices such as but not limited to X-Ray, CT, ultra-sound (US), etc. The radio opaque encasement markings 104 are also applicable in the case of joined markers. The connection between joined markers can also be uniquely formed and identifiable. The markers (a single or a joint marker) may be comprised of either or both external antenna/e and attached EIE/s, each with unique identifying shapes visible on imaging systems.

Another example group 120 demonstrates pairs of joined-markers. The joined-markers 120 are self-anchored by an expandable, retractable direct spring 122 or by an expandable retractable pre-bent spring 124. The spring can be made of bio-compatible diamagnetic metal, nitinol or tungsten for example. In some embodiments the spring 122 or 124 may serve as an external part of the antenna of its associated pair of markers. For example, as part of the dipole of a dual-frequency antenna.

A third group 130 demonstrates other pairs of joined-markers. The joined-markers 130 are self-anchored by a fixed direct spring 132 or a fixed pre-bent spring 134. The fixed spring can be made of bio-compatible diamagnetic metal, nitinol or tungsten for example. In some embodiments the fixed direct spring 132 or the fixed pre-bend spring 134 may serve as an external part of a dual-frequency antenna of its associated pair of markers.

The connection of markers with fixed, expandable, retractable, direct and pre-bent springs (being antenna/e and or EIE/s) as described above would be applicable to all forms and combinations of markers such as but not limited to markers comprised of a capsule, markers comprised of a reflective material which can be a metal or combination of metals and markers comprised of a card with a unique ID.

Figure 2:
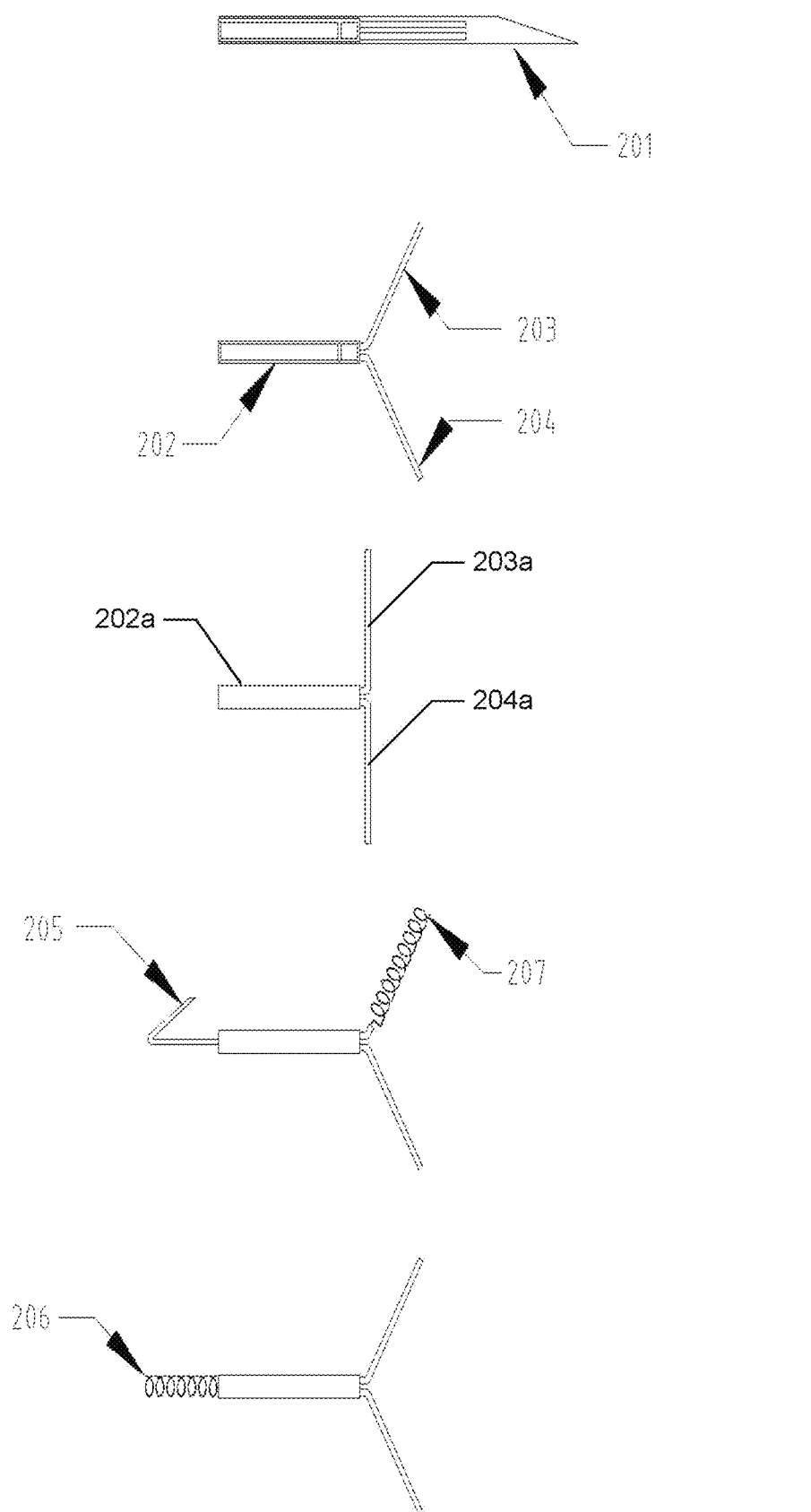
FIG. 2 schematically illustrates examples of markers with different configurations and shapes of antennae and/or EIE's.

FIG. 2 illustrates example embodiments of makers comprising folding dipole antennae. Such example embodiments may comprise a capsule 202 or 202a associated with two folding arms 203 and 204 and 203a and 204a (respectively) of a dipole antenna. Wherein the marker is configured to be situated within the lumen of a needle 201 and can be deployed from the needle 201. The antennae are designed to assume varying angles of orientation to each other on deployment from the needle 201. The two arms 203 and 204 are configured to be opened at an angle of 120 degrees to each other, for example; while arms 203a and 204a are configured to open at an angle of 180 degrees to each other, for example. In some embodiments of the disclosed technique the marker's antennae and attached EIE's can be of differing configurations and shapes. The antennae can be in the form of a spring 207, and the EIE's can be in the form of a hook 205 or a spring 206, for example.

The markers that are illustrated in FIG. 2 can be made of materials similar to the materials that are disclosed above in conjunction with FIG. 1. In addition, the markers that are related to FIG. 2 may comprise identification elements similar to the identification elements of the markers that are disclosed above in conjunction with FIG. 1. Further, the markers related to FIG. 2 can be configured to be associated as joined-markers as it is disclosed above. In the present disclosure and the claims, the terms joint-markers, joint marker, joined markers, joined-markers, and joined-marker may be used interchangeably.

In the description and claims of the present disclosure, each of the verbs, "comprise", "include", "have", and conjugates thereof, are used to indicate that the object or objects of the verb are not necessarily a complete listing of members, components, elements, or parts of the subject or subjects of the verb.

The present disclosure has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Many other ramification and variations are possible within the teaching of the embodiments comprising different combinations of features noted in the described embodiments.

It will be appreciated by persons skilled in the art that the present invention is not limited by what has been particularly shown and described herein above. Rather the scope of the invention is defined by the claims that follow.

The invention claimed is:

1. An apparatus, comprising:
   at least first and second markers configured for implantation within a breast of a patient so as to delineate different respective regions of interest within the breast,
   an elongate spring that joins the first marker to the second marker, wherein at least one of the first and second markers comprises an antenna and wherein the elongate spring is configured to serve as an external part of the antenna, and
   wherein the first and second markers are visually differentiable from each other in a pre-operative mammogram of the breast.

2. The apparatus according to claim 1, wherein the first and second markers are visually differentiable from each other at least by virtue of each of the first and second markers comprising a unique radio opaque marking.

3. The apparatus according to claim 1, wherein the first and second markers are visually differentiable from each other at least by virtue of each of the first and second markers comprising unique ridges on a surface of the respective marker.

4. The apparatus according to claim 1, wherein the first and second markers are visually differentiable from each other at least by virtue of each of the first and second markers comprising a respective radio-opaque coil winding having unique interspaced gaps.

5. The apparatus according to claim 1, wherein each of the first and second markers comprises a respective antenna and wherein the first and second markers are visually differentiable from each other at least by virtue of each of the respective antennas having a unique shape.

6. The apparatus according to claim 1, wherein the first and second markers comprise respective clips, and wherein the first and second markers are visually differentiable from each other at least by virtue of the clips.

7. The apparatus according to claim 1, wherein the first and second markers comprise respective rings, and wherein the first and second markers are visually differentiable from each other at least by virtue of the rings.

8. The apparatus according to claim 1, wherein the antenna comprises a dual frequency antenna, and wherein the elongate spring is configured to serve as part of a dipole of the antenna.

9. The apparatus according to claim 1, wherein the elongate spring is expandable and retractable.

10. The apparatus according to claim 1, wherein the elongate spring is fixed.

11. The apparatus according to claim 1, wherein each of the first and second markers is aligned in parallel with the spring.

12. The apparatus according to claim 1, wherein each of the first and second markers is not aligned in parallel with the elongate spring.

13. The apparatus according to claim 1, wherein the antenna has a visually recognizable shape.

14. The apparatus according to claim 1, wherein the first marker and second marker are of different functional types.

15. The apparatus according to claim 1, wherein each of the first and second markers comprises a microelectronic chip.

16. The apparatus according to claim 15, wherein the microelectronic chip stores an electronic representation of a unique collective ID of a respective marker of the first and second markers.

17. The apparatus according to claim 1, wherein the first and second markers are visually differentiable from each other by at least two features.

18. The apparatus according to claim 17, wherein the first and second markers are visually differentiable from each other by a body shape of respective bodies of the first and second markers and an attachment shape of respective attachments to the bodies.

19. A method, comprising:
   prior to a pre-operative mammogram of a breast of a patient, in which breast is implanted a first marker such that the first marker delineates a first region of interest within the breast, selecting a second marker; and
   implanting the second marker in the breast, thereby delineating a second region of interest within the breast;
   wherein the method is performed using:
   at least the first and second markers, the first and second markers being configured for implantation within the patient's breast so as to delineate different respective regions of interest within the breast,
   an elongate spring that joins the first marker to the second marker, wherein at least one of the first and second markers comprises an antenna and wherein the elongate spring is configured to serve as an external part of the antenna, and
   wherein the first and second markers are visually differentiable from each other in a pre-operative mammogram of the breast.

20. A method, comprising:
   identifying a lesion within a body of a patient; and
   bracketing an extent of the lesion for surgical removal, by implanting, within the body, a joint marker including first and second markers joined by an elongate spring;
   wherein the method is performed using the joint marker comprising:
   at least the first and second markers, the first and second markers being configured for implantation within the patient's breast so as to delineate different respective regions of interest within the breast,
   the elongate spring, the elongate spring joining the first marker to the second marker,
   wherein at least one of the first and second markers comprises an antenna and wherein the elongate spring is configured to serve as an external part of the antenna, and
   wherein the first and second markers are visually differentiable from each other in a pre-operative mammogram of the breast.

* * * * *